United States Patent
Sechrist et al.

(10) Patent No.: US 9,051,230 B2
(45) Date of Patent: Jun. 9, 2015

(54) PROCESSES FOR PRODUCING PROPYLENE FROM PARAFFINS

(75) Inventors: Paul A. Sechrist, South Barrington, IL (US); Gregory Werba, Arlington Heights, IL (US); Mohamed Shakur, Hoffman Estates, IL (US); Steven Lankton, Wheeling, IL (US); Steven Kozup, Chicago, IL (US); Bing Sun, South Barrington, IL (US)

(73) Assignee: UOP LLC, Des Plaines, IL (US)

( * ) Notice: Subject to any disclaimer, the term of this patent is extended or adjusted under 35 U.S.C. 154(b) by 83 days.

(21) Appl. No.: 13/090,783

(22) Filed: Apr. 20, 2011

(65) Prior Publication Data

US 2012/0271080 A1    Oct. 25, 2012

(51) Int. Cl.
| | | |
|---|---|---|
| *C07C 5/02* | (2006.01) | |
| *C07C 5/22* | (2006.01) | |
| *C07C 11/06* | (2006.01) | |
| *C07C 9/12* | (2006.01) | |
| *C07C 5/27* | (2006.01) | |
| *C07C 5/333* | (2006.01) | |

(52) U.S. Cl.
CPC ............ *C07C 5/2732* (2013.01); *C07C 5/3337* (2013.01); *C07C 2523/42* (2013.01)

(58) Field of Classification Search
CPC ............ C07C 11/06; C07C 9/10; C07C 9/12; C07C 5/02; C07C 5/22
USPC .......................... 585/315, 324, 654, 655, 664
See application file for complete search history.

(56) References Cited

U.S. PATENT DOCUMENTS

| | | | |
|---|---|---|---|
| 2,461,153 A | 2/1949 | Goldsby | |
| 3,434,959 A | 3/1969 | Kirk, Jr. | |
| 4,324,937 A * | 4/1982 | Vora | 585/315 |
| 4,347,399 A | 8/1982 | Rice | |
| 4,356,014 A * | 10/1982 | Higgins | 62/622 |
| 4,868,342 A * | 9/1989 | Verson | 568/697 |
| 2008/0242904 A1* | 10/2008 | Rice et al. | 585/311 |
| 2009/0069617 A1* | 3/2009 | Shecterle et al. | 585/738 |

FOREIGN PATENT DOCUMENTS

WO         9321138         10/1993

OTHER PUBLICATIONS

Mauhar, S.M., Barjaktarovic, B.G., and Sovilj, M. N., Optimization of Propylene-Propane Distillation Process, 2004.*
Tanguay, D., et al., Integrating the cryogenic recovery unit [(CRU)] into an overall process design of an iso-butane dehydrogenation unit, AIChE 1994 Spring National Meeting (Atlanta Apr. 17-21, 1994) Preprint N.70b 17P, Apr. 17, 1994.

* cited by examiner

*Primary Examiner* — In Suk Bullock
*Assistant Examiner* — Philip Louie

(57) ABSTRACT

Embodiments of processes for producing propylene from paraffins are provided. The process comprises the steps of combining an effluent that comprises propylene and propane from a paraffin dehydrogenation reactor with an offgas stream that comprises propane to form a combined effluent stream. The combined effluent stream is separated into a propylene product stream and a propane-rich recycle stream. The propane-rich recycle stream is introduced to the paraffin dehydrogenation reactor operating at dehydrogenation conditions to convert propane in the propane-rich recycle stream to propylene.

7 Claims, 3 Drawing Sheets

PROCESSES FOR PRODUCING PROPYLENE FROM PARAFFINS

FIELD OF THE INVENTION

The present invention relates generally to processes for producing light olefins from paraffins, and more particularly relates to processes for producing propylene from the catalytic dehydrogenation of paraffins such as propane.

BACKGROUND OF THE INVENTION

Catalytic dehydrogenation processes are commonly used for the production of light olefins by conversion from their corresponding paraffins. One specific application of this technology produces propylene from the conversion of propane. Propylene is one of the world's largest produced petrochemical commodities and is used, for example, in the production of polypropylene, acrylonitrile, acrylic acid, acrolein, propylene oxide, glycols, plasticizers, oxo alcohols, cumene, isopropyl alcohol, and acetone.

The growth in propylene production is primarily driven by the industry demand for polypropylene. Polypropylene is used in such everyday products as packaging materials and outdoor clothing. The growth rate of polypropylene is expected to be about 5% per year for the near future. To meet this growing demand, producers of propylene are looking for ways to increase their propylene production preferably with minimal additional equipment and cost.

Accordingly, it is desirable to provide processes for increasing production of propylene from paraffins. Moreover, it is desirable to provide processes for increasing production of propylene from paraffins with minimal additional equipment and cost. Furthermore, other desirable features and characteristics of the present invention will become apparent from the subsequent Detailed Description of the Invention and the appended Claims, when taken in conjunction with the accompanying drawings and this Background of the Invention.

SUMMARY OF THE INVENTION

Processes for producing propylene from paraffins are provided herein. In accordance with an exemplary embodiment, a process for producing propylene from paraffins comprises the steps of combining an effluent that comprises propylene and propane from a paraffin dehydrogenation reactor with an offgas stream that comprises propane to form a combined effluent stream. The combined effluent stream is separated into a propylene product stream and a propane-rich recycle stream. The propane-rich recycle stream is introduced to the paraffin dehydrogenation reactor operating at dehydrogenation conditions to convert propane in the propane-rich recycle stream to propylene.

In accordance with another exemplary embodiment, a process for producing propylene from paraffins is provided. The process comprises the steps of feeding n-butane to a butane isomerization process to form an iso-butane product stream and an offgas stream that comprises propane. Propane is fed to a paraffin dehydrogenation reactor that is operating at dehydrogenation conditions to produce an effluent that comprises propylene and propane. The effluent is combined with the offgas stream to form a combined effluent stream. The combined effluent stream is separated into a propylene product stream and a propane-rich recycle stream. The propane-rich recycle stream is introduced to the paraffin dehydrogenation reactor to convert propane in the propane-rich recycle stream to propylene.

BRIEF DESCRIPTION OF THE DRAWINGS

Embodiments of the present invention will hereinafter be described in conjunction with the following drawing figures, wherein like numerals denote like elements, and wherein.

DETAILED DESCRIPTION

Figure 1:
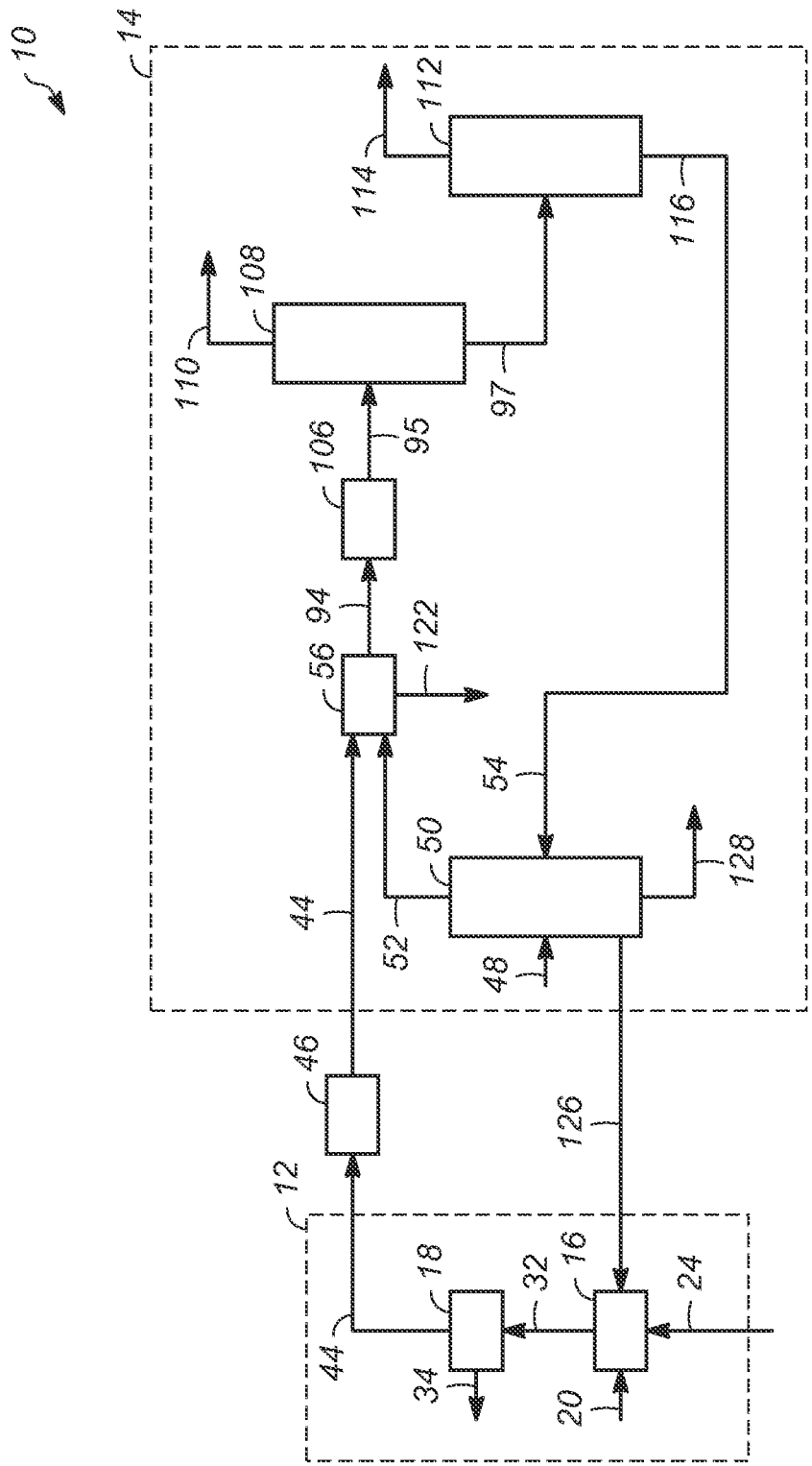
FIG. 1 schematically illustrates an apparatus for producing propylene from paraffins in accordance with an exemplary embodiment.

The following Detailed Description is merely exemplary in nature and is not intended to limit the invention or the application and uses of the invention. Furthermore, there is no intention to be bound by any theory presented in the preceding Background of the Invention or the following Detailed Description.

Various embodiments contemplated herein relate to processes for producing propylene from paraffins such as propane. A fresh propane feed is introduced to a paraffin dehydrogenation reactor that contains dehydrogenation catalyst and is operating at dehydrogenation conditions to produce an effluent. The effluent contains propylene, unconverted propane, hydrogen, and various other hydrocarbons such as $C_2-$, $C_4+$, and some dienes and alkynes. As used herein, $C_x$ means hydrocarbon molecules that have "X" number of carbon atoms, $C_x+$ means hydrocarbon molecules that have "X" and/or more than "X" number of carbon atoms, and $C_x-$ means hydrocarbon molecules that have "X" and/or less than "X" number of carbon atoms. An offgas stream containing at least some propane is combined with the effluent to form a combined effluent stream that contains the additional propane from the offgas stream. Preferably, the offgas stream, e.g., a waste or tail gas stream for burning and the like, is formed from another process in the plant that is being used to produce, for example, a valuable product stream.

In an exemplary embodiment, the offgas stream is produced from a paraffin isomerization process, such as, for example, a butane isomerization process that converts n-butane to iso-butane. The butane isomerization process includes an isomerization reactor that converts an n-butane feed to an iso-butane-rich stream that is separated via a distillation column or the like into an iso-butane product stream and an offgas stream. The offgas stream contains propane, hydrogen, some n-butane and/or iso-butane, and other various light hydrocarbons, such as, for example, $C_2-$, $C_5+$, and the like.

The effluent from the paraffin dehydrogenation reactor is compressed to a predetermined high pressure prior to being combined with the offgas stream that is preferably at a similar or greater pressure than the compressed effluent. The offgas stream and the effluent are combined to form a combined effluent stream that is subsequently cooled and separated to form a propylene product stream and a propane-rich recycle stream. The propane-rich recycle stream is then introduced to the paraffin dehydrogenation reactor along with additional fresh propane feed. Because the propane-rich recycle stream contains additional propane from the paraffin isomerization process, more propane is available in the paraffin dehydrogenation reactor for conversion to propylene compared to conventional processes, thereby increasing the amount of propylene product produced. Moreover, minimal additional equipment and/or cost are needed to fluidly couple the paraffin isomerization process to the effluent section of the paraffin dehydrogenation process.

Referring to FIG. 1, a schematic depiction of an apparatus 10 for producing propylene from paraffins in accordance with an exemplary embodiment is provided. The apparatus 10 comprises a paraffin isomerization section 12 and a paraffin dehydrogenation section 14. The paraffin isomerization section 12 is configured as a butane isomerization process for converting n-butane to iso-butane. The paraffin dehydrogenation section 14 is configured as a catalytic dehydrogenation process for converting propane to propylene. The paraffin isomerization section 12 comprises a reactor section 16 and a stabilizers section 18.

Figure 2:
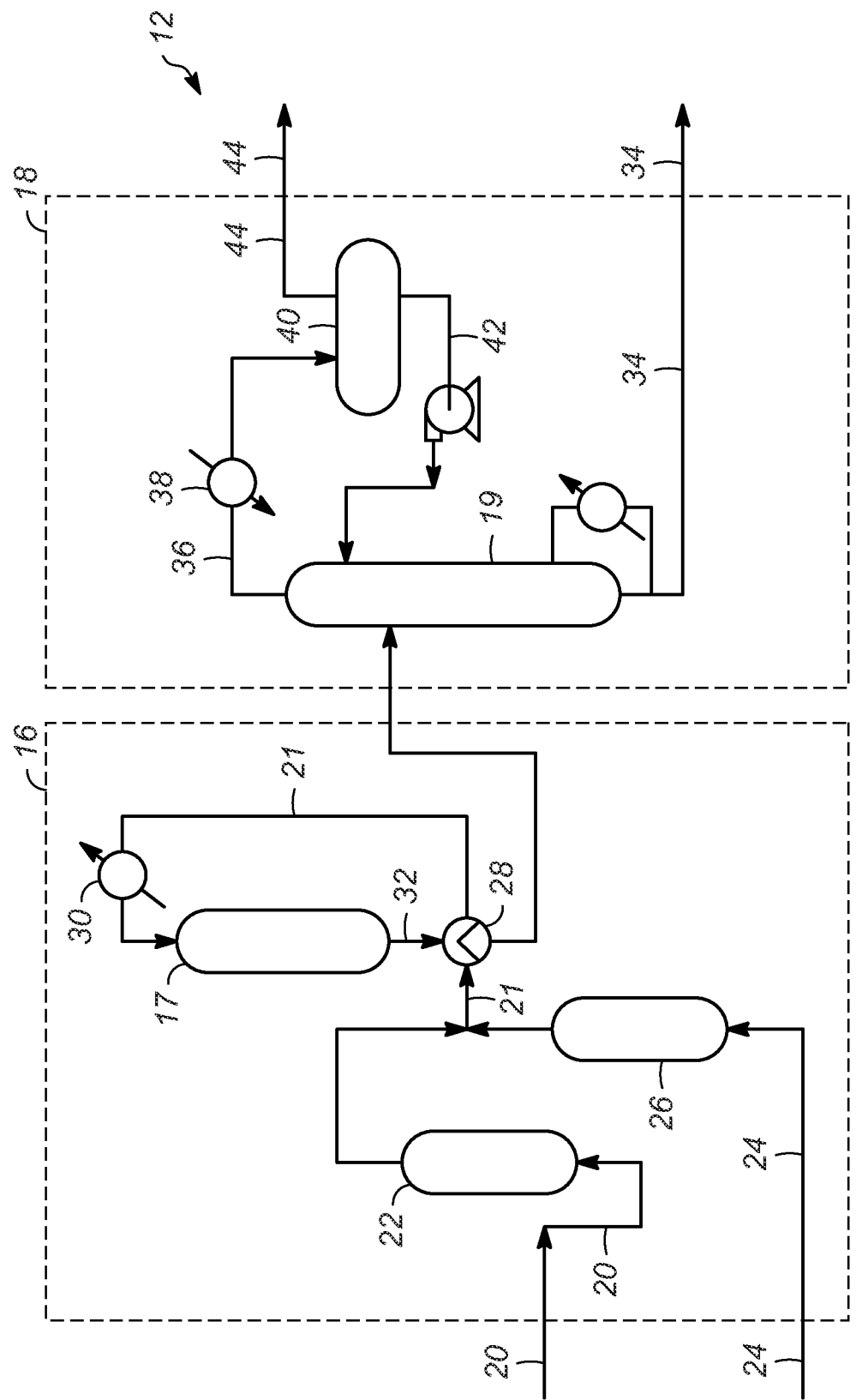
FIG. 2 schematically illustrates a paraffin isomerization section of the apparatus depicted in FIG. 1.

FIG. 2 is a detailed illustration of paraffin isomerization section 12. The reactor section 16 and the stabilizer section 18 of paraffin isomerization section 12 include a reactor 17 and a distillation column 19, respectively, that are in fluid communication. As illustrated, a feed stream 20, which is preferably rich in n-butane and may also contain relatively small amounts of iso-butane, pentanes, and heavier materials, is passed through a dryer 22 for removing water. A hydrogen feed 24 is passed through a dryer 26 for removing water and is combined with the dried n-butane rich stream to form a combined stream 21. The combined stream 21 is passed through a heat exchanger 28 and a heater 30, and is introduced to the reactor 17.

In an exemplary embodiment, the reactor 17 is a fixed-bed catalytic reactor operating at a temperature of about 90 to about 150° C. and containing a high-activity chloride-promoted catalyst to isomerize n-butane to iso-butane to produce an iso-butane-rich stream 32. The iso-butane-rich stream 32 is passed through the heat exchanger 28 and is introduced to the distillation column 19 that separates the iso-butane-rich stream 32 into an iso-butane product stream 34 as, for example, a bottom stream and a LPG (liquefied petroleum gas) stream 36 as, for example, an overhead stream. The LPG stream 36 is passed through a cooler 38 and is introduced to a vent drum 40. A liquid stream 42 is removed from the bottom of the vent drum 40 and is passed back to the distillation column 19 for reflux.

Light volatiles are removed from the vent drum 40 and form an offgas stream 44. The offgas stream 44 contains propane, hydrogen, some n-butane and/or iso-butane, and other various light hydrocarbons, such as, for example, $C_2-$, $C_5+$, and the like. In an exemplary embodiment, the offgas stream 44 is vented from the vent drum 40 at a relatively high pressure of from about 1,000 to about 2,000 kPa. Referring back to FIG. 1, the offgas stream 44 may optionally be passed through a scrubber 46 to remove any chloride containing compounds, such as, for example, hydrogen chloride that may have been formed during interaction with the high-activity chloride-promoted catalyst in the reactor 17. Alternatively, any chloride containing compounds may be removed from the offgas stream 44 downstream in the paraffin dehydrogenation section 14 as will be discussed in further detail below.

A fresh propane feed 48 is passed through a feed guard bed (not shown) and a feed dryer (not shown) before being directed to a depropanizer unit 50 (e.g. single or multiple column) for $C_4+$ removal. The feed guard bed removes organic metal compounds and the feed dryer removes nitrogen compounds and water from the fresh propane feed 48 to protect downstream catalyst and reactor performance and to form a treated propane feed 52.

Figure 3:
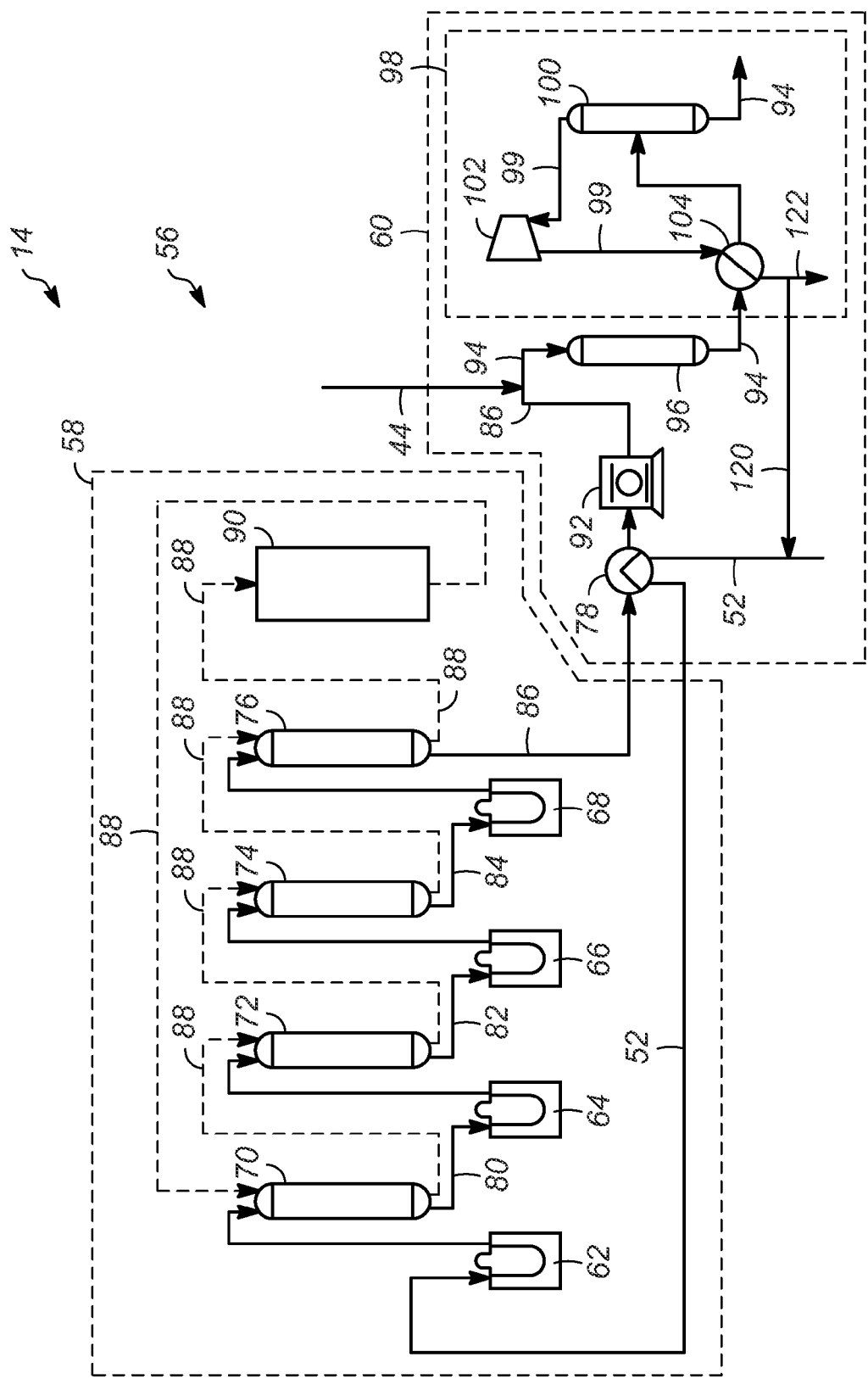
FIG. 3 schematically illustrates a paraffin dehydrogenation reactor and effluent section of the apparatus depicted in FIG. 1.

The treated propane feed 52 is introduced to a dehydrogenation reactor and effluent section 56. FIG. 3 is a detailed illustration of the dehydrogenation reactor and effluent section 56 in accordance with an exemplary embodiment. The dehydrogenation reactor and effluent section 56 comprises a reactor section 58 in fluid communication with an effluent section 60. As illustrated, the reactor section 58 comprises four fired heaters 62, 64, 66, and 68 and four moving bed reactors 70, 72, 74, and 76 alternately connected in series. The four moving bed reactors 70, 72, 74, and 76 each contain dehydrogenation catalyst, e.g., platinum-containing catalyst and the like, and are configured to advance the dehydrogenation catalyst as moving beds between the reactors 70, 72, 74, and 76 as is well known in the art. Other reactor arrangements for dehydrogenation of paraffins, such as, for example, swing bed reactor arrangements and the like may also be used.

The treated propane feed 52 is passed through a heat exchanger 78 to the first fired heater 62 that provides the necessary thermal energy for converting a first portion of the propane in the treated propane feed 52 to propylene via a one-step endothermic dehydrogenation reaction in the first reactor 70 to form a partially reacted stream 80. In an exemplary embodiment, the four moving bed reactors 70, 72, 74, and 76 are operating at a temperature of from about 575 to about 675° C. and at a relatively low pressure of within about a few 100 kPa of atmospheric pressure. The partially reacted stream 80 is passed along from the first reactor 70 to the second fired heater 64 and reactor 72 for further conversion of propane to propylene to form a second partially reacted stream 82. The second partially reacted stream 82 is passed along to the third fired heater 66 and third reactor 74 for further conversion of propane to propylene to form a third partially reacted stream 84 that is then passed along to the fourth fired heater 68 and fourth reactor 76 for further conversion of propane to propylene to form an effluent 86.

In an exemplary embodiment, the effluent 86 contains propylene, unconverted propane, hydrogen, and various other hydrocarbons such as $C_2-$, $C_4+$, and some dienes and alkynes. As indicated by the dashed lines 88, partially spent dehydrogenation catalyst is transferred from the first reactor 70 progressively to each of the next reactors 72, 74, and 76 in a moving bed fashion for further conversion of propane to propylene, and is then sent to a regeneration unit 90 for regeneration of the spent dehydrogenation catalyst. The regenerated dehydrogenation catalyst is then transferred from the regeneration unit 90 back to the first reactor 70 to replenish partially spent catalyst that is being removed from the first reactor 70.

As illustrated, the effluent 86 is passed from the reactor section 58 to the effluent section 60 where the effluent 86 is partially cooled via a heat exchanger 78. The effluent 86 is then passed to a compressor 92 that compresses the effluent 86 to a predetermined high pressure. In an exemplary embodiment, the effluent 86 is compressed to a predetermined high pressure of from about 1,000 to about 2,000 kPa.

The offgas stream 44 is combined with the effluent 86 in the effluent section 60 to form a combined effluent stream 94. In an exemplary embodiment, the offgas stream 44 is at about the same pressure or greater than the pressure of the effluent 86 after being compressed to the predetermined high pressure. Preferably, the offgas stream 44 is combined with the effluent 86 downstream from the compressor 92 as illustrated. However, although the offgas stream 44 is shown as being combined with the effluent 86 downstream from the compressor 92, it should be understood that the offgas stream 44 can alternatively be combined with the effluent 86 upstream from the compressor 92.

The combined effluent stream 94 is dried and treated by removing any chloride containing compounds via a chloride treater and dryer unit 96. The combined effluent stream 94 is then passed along to the cold box section 98 of the effluent section 60. As illustrated, the cold box section 98 comprises a separator 100, an expander 102, and a heat exchanger 104 that are cooperatively configured to cryogenically cool the combined effluent stream 94. In particular, hydrogen is removed from the combined effluent stream 94, which is a mixed vapor-liquid phase, downstream in the separator 100 as, for example, an overhead stream and is expanded via the expander 102 to form a chilled hydrogen stream 99. The upstream combined effluent stream 94 is cryogenically cooled via indirect heat exchange with the chilled hydrogen stream 99 in the heat exchanger 104 and is removed from the effluent section 60 as, for example, a liquid bottom stream from the separator 100. In an exemplary embodiment, the combined effluent stream 94 is cooled to a temperature of from about −130 to about −150° C. As illustrated, the chilled hydrogen stream 99 is split downstream from the heat exchanger 104 into a hydrogen recycle stream 120 that is combined with the treated propane feed 52 to provide fuel for the first fired heater 62, and a second hydrogen stream 122 that is removed from the dehydrogenation reactor and effluent section 56.

Referring again to FIG. 1, the combined effluent stream 94 is passed along to a selective hydrogenation reactor 106 where methyl acetylene and other triple bond hydrocarbons and dienes contained in the combined effluent stream 94 are saturated to enhance the purity and to form a first treated combined effluent stream 95. The first treated combined effluent stream 95 is then introduced to the deethanizer unit 108 for removal of $C_2-$ hydrocarbons as, for example, an overhead stream 110 and to form a second treated combined effluent stream 97. The second treated combined effluent stream 97 is removed from the deethanizer unit 108 as, for example, a bottom stream and is passed along to the propylene-propane splitter unit 112. The propylene-propane splitter unit 112 separates the second treated combined effluent stream 97 into a propylene product stream 114 as, for example, an overhead stream and a propane-rich recycle stream 116 as, for example, a bottom stream.

The propane-rich recycle stream 116 is advanced to the depropanizer unit 50 and is mixed with the fresh propane feed 48. In an exemplary embodiment, the depropanizer unit 50 removes heavier hydrocarbons from the combined fresh propane feed 48 and the propane-rich recycle stream 116. As illustrated, the heavier hydrocarbons are separated and removed as a $C_4$ hydrocarbon stream 126 and a $C_5+$ hydrocarbon stream 128. In a preferred embodiment, the $C_4$ hydrocarbon stream 126 is passed along to the reactor section 16 of the paraffin isomerization section 12 for conversion with the n-butane feed 20 to increase the amount of iso-butane contained in the iso-butane product stream 34.

Accordingly, processes for producing propylene from paraffins such as propane have been described. The various embodiments comprise feeding fresh propane to a paraffin dehydrogenation reactor that contains dehydrogenation catalyst and is operating at dehydrogenation conditions to produce an effluent. The effluent contains propylene, unconverted propane, hydrogen, and various other hydrocarbons such as $C_2-$, $C_4+$, and some dienes and alkynes. An offgas stream containing at least some propane is combined with the effluent to form a combined effluent stream that contains the additional propane from the offgas stream. The combined effluent stream is cooled and separated to form a propylene product stream and a propane-rich recycle stream. The propane-rich recycle stream is then introduced to the paraffin dehydrogenation reactor along with additional fresh propane feed. Because the propane-rich recycle stream contains additional propane from the paraffin isomerization process, more propane is available in the paraffin dehydrogenation reactor for conversion to propylene compared to conventional process, thereby increasing the amount of propylene product produced. Moreover, minimal additional equipment and/or cost are needed to fluidly couple the paraffin isomerization process to the effluent section of the paraffin dehydrogenation process.

While at least one exemplary embodiment has been presented in the foregoing Detailed Description, it should be appreciated that a vast number of variations exist. It should also be appreciated that the exemplary embodiment or exemplary embodiments are only examples, and are not intended to limit the scope, applicability, or configuration of the invention in any way. Rather, the foregoing Detailed Description will provide those skilled in the art with a convenient road map for implementing an exemplary embodiment of the invention, it being understood that various changes may be made in the function and arrangement of elements described in an exemplary embodiment without departing from the scope of the invention as set forth in the appended Claims and their legal equivalents.

What is claimed is:

1. A process for producing propylene from paraffins, the process comprising the steps of:

combining an effluent comprising propylene and propane from a paraffin dehydrogenation reactor with an offgas stream from a butane isomerization process comprising propane and hydrogen to form a combined effluent stream;

passing the combined effluent stream through a chloride treater and dryer unit to generate a treated combined effluent stream;

separating the hydrogen from the treated combined effluent stream to form a hydrogen stream and passing the hydrogen stream to the paraffin dehydrogenation reactor;

separating a remainder of the treated combined effluent stream into a propylene product stream and a propane-rich recycle stream;

passing the propane-rich recycle stream to a separation unit to generate a propane rich-overhead stream, and a C4+ bottoms stream;

passing the $C_{4+}$ bottoms stream to a second separation unit to generate a $C_4$ stream and a $C_{5+}$ stream;

passing the $C_4$ stream to the butane isomerization process to generate the offgas stream from the butane isomerization process comprising hydrogen; and introducing the propane-rich overhead stream to the paraffin dehydrogenation reactor operating at effective dehydrogenation conditions to produce the effluent comprising propylene and propane.

2. The process according to claim 1, further comprising a step of compressing the effluent from the paraffin dehydrogenation reactor to a predetermined pressure in a range of from about 1,000 to 2,000 kPa.

3. The process according to claim 2, wherein the offgas stream is at a pressure of about or greater than the predetermined pressure, and the step of compressing occurs prior to the step of combining the effluent from the paraffin dehydrogenation reactor with the offgas.

4. The process according to claim 1, further comprising a step of cooling the treated combined effluent stream to a predetermined temperature in a range of from about −130 to about −150 °C.

5. The process according to claim 4, wherein the treated combined effluent stream comprises $C_{2-}$ hydrocarbons, and further comprising removing the $C_{2-}$ hydrocarbons from the treated combined effluent stream after the step of cooling the treated combined effluent stream.

6. The process according to claim 4, wherein the treated combined effluent stream comprises $C_{4+}$ hydrocarbons, and further comprising removing the $C_{4+}$ hydrocarbons from the treated combined effluent stream after the step of cooling the treated combined effluent stream.

7. The process according to claim 6, further comprising separating the removed $C_{4+}$ hydrocarbons to form a $C_4$ hydrocarbons stream and a $C_{5+}$ hydrocarbon stream.

* * * * *